United States Patent

Tanaka et al.

[11] Patent Number: 5,912,362
[45] Date of Patent: Jun. 15, 1999

[54] PROCESS FOR PRODUCING ISOCHROMAN COMPOUNDS

[75] Inventors: Shigeyoshi Tanaka; Masayuki Oku; Junji Koshino, all of Wakayama, Japan

[73] Assignee: Kao Corporation, Tokyo, Japan

[21] Appl. No.: 08/945,798

[22] PCT Filed: Apr. 22, 1996

[86] PCT No.: PCT/JP96/01088

§ 371 Date: Nov. 10, 1997

§ 102(e) Date: Nov. 10, 1997

[87] PCT Pub. No.: WO96/35684

PCT Pub. Date: Nov. 14, 1996

[30] Foreign Application Priority Data

May 10, 1995 [JP] Japan ..................... 7-111543

[51] Int. Cl.⁶ ................. C07D 311/76; C07D 311/78; C07D 311/92
[52] U.S. Cl. ........... 549/384; 549/385; 549/389; 549/398; 549/408; 549/409
[58] Field of Search ................... 549/384, 385, 549/389, 398, 408, 409

[56] References Cited

U.S. PATENT DOCUMENTS 3,360,530 12/1967 Heeringa et al. ............. 260/345.2
3,532,719 10/1970 Theimer ..................... 260/345.2

FOREIGN PATENT DOCUMENTS 47-42836 10/1972 Japan .
63-10782 1/1988 Japan .
1 552 004 9/1979 United Kingdom .

Primary Examiner—Richard L. Raymond
Assistant Examiner—Ann M. Kessinger
Attorney, Agent, or Firm—Oblon, Spivak, McClelland, Maier & Neustadt, P.C.

[57] ABSTRACT

High-purity isochroman compounds can be obtained in high yields according to a simple and economical process for preparing isochroman compounds, comprising the step of adding an aqueous solution of formaldehyde having a concentration of 40 to 70 wt. % to a complex of an arylalkanol represented by the following general formula (II) with a Friedel-Crafts catalyst to cyclize the arylalkanol:

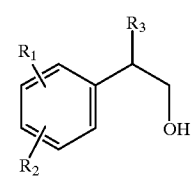

(II)

wherein $R_1$ and $R_2$ each stands for a hydrogen atom, a lower alkyl group or a lower alkoxyl group, or alternatively $R_1$ and $R_2$ are respectively bonded to adjacent carbon atoms with mutual bonding of $R_1$ and $R_2$ together with the carbon atoms respectively bonded to $R_1$ and $R_2$ to form a benzene ring, a naphthalene ring, or a $C_5$ or $C_6$ cycloalkane or cycloalkene which may have 1 to 6 lower alkyl groups; and $R_3$ stands for a hydrogen atom or a lower alkyl group.

6 Claims, No Drawings

PROCESS FOR PRODUCING ISOCHROMAN COMPOUNDS

BACKGROUND OF THE INVENTION

1. Field of the Invention

The present invention relates to a process for preparing isochroman compounds using an aqueous solution of formaldehyde having a specific concentration as a formaldehyde source. The process of the present invention is simplified and economical.

2. Description of Related Art

It has been known to date that isochroman compounds represented by the following general formula (I) have an excellent musky odor:

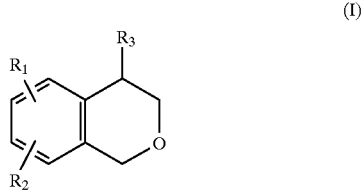

(I)

wherein $R_1$ and $R_2$ each stands for a hydrogen atom, a lower alkyl group or a lower alkoxyl group, or alternatively $R_1$ and $R_2$ are respectively bonded to adjacent carbon atoms with mutual bonding of $R_1$ and $R_2$ together with the carbon atoms respectively bonded to $R_1$ and $R_2$ to form a benzene ring, a naphthalene ring, or a $C_5$ or $C_6$ cycloalkane or cycloalkene which may have 1 to 6 lower alkyl groups; and $R_3$ stands for a hydrogen atom or a lower alkyl group.

Examples of the processes for preparing such isochroman compounds include:

(1) a process comprising introducing hydrogen chloride gas into a mixture of an arylalkanol and paraformaldehyde;

(2) a process comprising reacting an aromatic hydrocarbon compound with an alkylene oxide in the presence of aluminum chloride to form a complex of an arylalkanol with aluminum chloride, partially deactivating the aluminum chloride in the complex with a substance containing a free hydroxyl group, and adding paraformaldehyde to the resulting reaction mixture to cyclize the arylalkanol;

(3) a process comprising reacting an arylalkanol with an acetal in the presence of a protonic acid;

(4) an improvement of the process described in the above item (3), comprising effecting the reaction in the presence of an azeotropic agent such as n-hexane, cyclohexane, methylcyclohexane, benzene or toluene;

(5) a process comprising adding chloride or oxychloride of sulfur or phosphorus to a mixture of an arylalkanol, concentrated hydrochloric acid and a compound capable of releasing formaldehyde; and (6) a process comprising reacting an arylalkanol with formaldehyde in the presence of a lower carboxylic acid anhydride or a methylene(lower carboxylate) having lower alkyl moieties in the acyl groups thereof and an acid catalyst at a high temperature.

Since the these process involve respective demerits, however, they are not well satisfactory as a process for preparing isochroman compounds.

More specifically, the process of the above item (1) involves disadvantages such as complicated operations, the necessity for the use of expensive and intractable hydrogen chloride gas, and the necessity for the removal of water formed in keeping with the progress of the reaction out of the reaction system because of the incapability of completing the reaction at the removal of water while lowering the yield and involving side reactions.

On the other hand, the process of the above item (2) involves disadvantages such as generation of hydrogen chloride gas in an intermediate treatment step (the step of partially deactivating aluminum chloride in the complex), the necessity for the use of a limited amount of a deactivator, a low yield resulting from incompletion of the reaction and occurrence of side reactions, and complicated operations in a post-treatment step (the step of recovering the reaction product).

Further, the process of the above item (3) involves disadvantages such as attainment of only an unsatisfactory yield despite the reaction effected at a high temperature over a long time according to this process, while the process of the above item (4) as an improvement thereof involves demerits such as a considerable cost involved in the recovery of an isochroman compound as the reaction product because of the use of an azeotropic agent.

Furthermore, the process of the above item (5) involves disadvantages such as generation of hydrogen chloride gas in the reaction system and attainment of only an unsatisfactory yield. On the other hand, the process of the above item (6) involves problems of complicated operations resulting from a high pressure of the reaction system because of the high-temperature reaction, and the necessity for the removal of the formed lower carboxylic acid out of the reaction system, as well as a demerit of attainment of only an unsatisfactory yield.

In view of the foregoing circumstances, the applicant has attempted the development of an improved process for preparing isochroman compounds. As a result, the applicant has found out and disclosed an improved process for preparing isochroman compounds whereby isochroman compounds can be prepared simply in good yields [see Japanese Patent Laid-Open No. 10,782/1988 (published on Jan. 18, 1988)]. This process comprises reacting an arylalkanol with formaldehyde or a compound capable of releasing formaldehyde in a chlorinated hydrocarbon solvent in the presence of a Friedel-Crafts catalyst having a dehydrating power.

Since, however, this process comprises first preparing an arylalkanol from an aromatic hydrocarbon compound, then separating it, and finally deriving an isochroman compound from the arylalkanol, it is complicated in steps and economically disadvantageous as compared with processes for synthesizing isochroman compounds directly from aromatic hydrocarbon compounds. Moreover, in carrying out this process, for example, paraformaldehyde is used as the compound capable of releasing formaldehyde. However, the production of powdery paraformaldehyde is doomed to be stopped because it deteriorates the working environment involved in the production thereof, while granular paraformaldehyde entails a situation that it cannot be dissolved in the reaction system and so scarcely advances the reaction.

DISCLOSURE OF THE INVENTION

SUMMARY OF THE INVENTION

An object of the present invention is to provide a process for preparing isochroman compounds whereby high-purity isochroman compounds can be obtained in high yields.

Another object of the present invention is to provide a simplified economical process for preparing isochroman compounds whereby high-purity isochroman compounds can be obtained in high yields.

The inventors of the present invention have made intensive investigations with a view to attaining the foregoing objects. As a result of those investigations, the inventors of the present invention have found out that high-purity isochroman compounds can be obtained in high yields when an aqueous solution of formaldehyde having a specific concentration is used as a formaldehyde source for a cyclization reaction. The inventors of the present invention have further found out that isochroman compounds can be prepared directly from aromatic hydrocarbon compounds through simple operations when an aqueous solution of formaldehyde having a specific concentration is used as the formaldehyde source while using the aromatic hydrocarbon compound as the starting material. The present invention has been completed based on these findings.

Specifically, the present invention provides a process for preparing isochroman compounds represented by the following general formula (I):

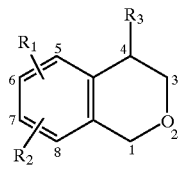

(I)

wherein $R_1$ and $R_2$ each stands for a hydrogen atom, a lower alkyl group or a lower alkoxyl group, or alternatively $R_1$ and $R_2$ are respectively bonded to adjacent carbon atoms with mutual bonding of $R_1$ and $R_2$ together with the carbon atoms respectively bonded to $R_1$ and $R_2$ to form a benzene ring, a naphthalene ring, or a $C_5$ or $C_6$ cycloalkane or cycloalkene which may have 1 to 6 lower alkyl groups; and $R_3$ stands for a hydrogen atom or a lower alkyl group;

comprising the step of adding an aqueous solution of formaldehyde having a concentration of 40 to 70 wt. % to a complex of an arylalkanol represented by the following general formula (II) with a Friedel-Crafts catalyst to cyclize the arylalkanol:

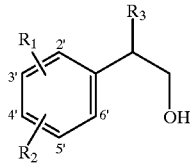

(II)

wherein $R_1$, $R_2$ and $R_3$ are each as defined above.

The foregoing process for preparing isochroman compounds may further comprise the step of mixing the arylalkanol of the above-mentioned formula (II) with the Friedel-Crafts catalyst to prepare the complex of the arylalkanol with the Friedel-Crafts catalyst.

Alternatively, the process for preparing isochroman compounds may further comprise the step of reacting an aromatic hydrocarbon compound represented by the following general formula (III) with an alkylene oxide in the presence of the Friedel-Crafts catalyst to prepare the complex of the arylalkanol with the Friedel-Crafts catalyst:

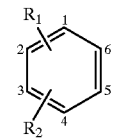

(III)

wherein $R_1$ and $R_2$ each stands for a hydrogen atom, a lower alkyl group or a lower alkoxyl group, or alternatively $R_1$ and $R_2$ are respectively bonded to adjacent carbon atoms with mutual bonding of $R_1$ and $R_2$ together with the carbon atoms respectively bonded to $R_1$ and $R_2$ to form a benzene ring, a naphthalene ring, or a $C_5$ or $C_6$ cycloalkane or cycloalkene which may have 1 to 6 lower alkyl groups.

The present invention, which is directed to a process for preparing isochroman compounds represented by the aforementioned formula (I), involves a process comprising the step of reacting an aromatic hydrocarbon compound represented by the above-mentioned formula (III) with an alkylene oxide in the presence of a Friedel-Crafts catalyst, and the step of adding an aqueous solution of formaldehyde having a concentration of 40 to 70 wt. % to the reaction mixture containing the resulting reaction product (i.e., the complex of the arylalkanol with the Friedel-Crafts catalyst) to cyclize the reaction product.

The scope and application of the present invention will become apparent from the following detailed description and Examples. Since, however, the spirit of the present invention as well as various alterations and modifications falling within the scope of the present invention would be apparent from the detailed description and Examples to those skilled in the art, it should be understood that the detailed description and Examples are described only by way of example although they demonstrate preferred embodiments of the present invention.

DETAILED DESCRIPTION OF THE INVENTION

In the aforementioned formulae (I), (II) and (III), the lower alkyl group in the definition of $R_1$, $R_2$ and $R_3$ refers to a $C_1$ to C6 linear or branched alkyl group, specific examples of which include a methyl group, an ethyl group, a propyl group, an isopropyl group, a butyl group, an isobutyl group, a pentyl group, an isopentyl group, a hexyl group, and an isohexyl group. Among them, a methyl group, an ethyl group, and an isopropyl group can be mentioned as preferred examples of the lower alkyl group. On the other hand, the lower alkoxyl group in the definition of $R_1$ and $R_2$ refers to an alkoxyl group derived from a $C_1$ to $C_6$ linear or branched alkyl group, specific examples of which include a methoxy group, an ethoxy group, a propoxy group, an isopropoxy group, a butoxy group, an isobutoxy group, a pentyloxy group, an isopentyloxy group, a hexyloxy group, and an isohexyloxy group. Among them, a methoxy group, an ethoxy group, and an isopropoxy group can be mentioned as preferred examples of the lower alkoxyl group.

In the aforementioned formulae (I), (II) and (III), possible one of the definition of $R_1$ and $R_2$ to the effect that $R_1$ and $R_2$ are respectively bonded to adjacent carbon atoms with mutual bonding of $R_1$ and $R_2$ together with the carbon atoms respectively bonded to $R_1$ and $R_2$ to form a benzene ring, a naphthalene ring, or a $C_5$ or $C_6$ cycloalkane or cycloalkene which may have 1 to 6 lower alkyl groups is intended to mean that a benzene ring together with $R_1$ and $R_2$ in these formulae represents a naphthalene ring, a phenanthrene ring, an anthracene ring, or a 1,2,3,4-pentahydronaphthalene ring or indane ring which may have 1 to 6 lower alkyl groups in a hydrogenated position(s) thereof. The expression "cycloalkane or cycloalkene" is used herein in order to indicate that the benzene ring in the aforementioned formulae may involve either 2 carbon atoms bonded to each other through a single bond or 2 carbon atoms bonded to each other through a double bond. The process of the present invention is especially preferably applicable to a compound wherein the $C_5$ or $C_6$ cycloalkane or cycloalkene which may have 1 to 6 lower alkyl groups is a cyclopentane or cyclohexane having 3 to 6 lower alkyl groups. A benzene ring, a naphthalene ring, or a cycloalkane or cycloalkene, formed by $R_1$ and $R_2$ together with the carbon atoms bonded thereto, may jointly own any two mutually adjacent carbon atoms at the 5,6-positions, 6,7-positions or 7,8-positions of the isochroman skeleton of the compound represented by the aforementioned formula (I), may jointly own any two mutually adjacent carbon atoms at the 2',3'-positions, 3',4'-positions or 4',5'-positions of the 2-phenylalkan-1-ol represented by the aforementioned formula (II), or may jointly own any two mutually adjacent carbon atoms at the 1,2-positions or 2,3-position of the benzene ring of the compound represented by the aforementioned formula (III).

Examples of the isochroman compounds of the aforementioned formula (I) prepared according to the process of the present invention include isochroman represented by the following formula (A), 6-oxa-1,1,2,3,3,8-hexamethyl-2,3,5,6,7,8-hexahydro-1H-benz[f]indene (galaxolide) represented by the following formula (B), 6-oxa-1,1,3,8-tetramethyl-3-ethyl-2,3,5,6,7,8-hexahydro-1H-benz[f]indene represented by the following formula (C), and 6-oxa-1,1,3,3,8-pentamethyl-2,3,5,6,7,8-hexahydro-1H-benz[f]-indene represented by the following formula (D):

(A)

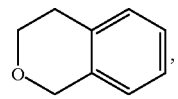

(B)

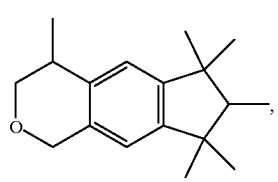

(C)

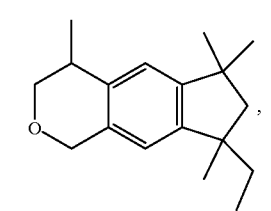

(D)

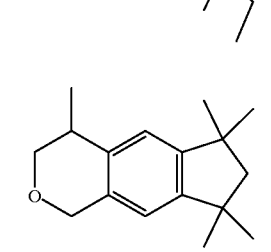

Examples of the arylalkanol of the aforementioned formula (II) to be used in the present invention include phenylethyl alcohol represented by the following formula (i), 2-(1',1',2'3',3'-pentamethylindan-5'-yl)-1-propanol represented by the following formula (ii), 2-(1'-ethyl-1,'3',3'-trimethylindan -5'-yl)-1-propanol represented by the following formula (iii), and 2-(1,',1',3',3'-tetramethylindan -5'-yl)-1-propanol represented by the following formula (iv):

(i)

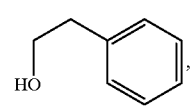

(ii)

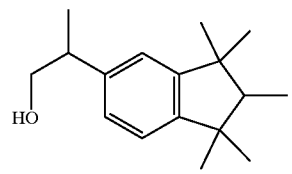

(iii)

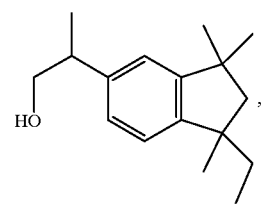

(iv)

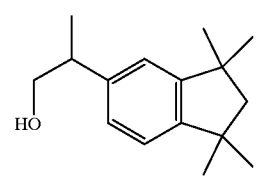

Examples of the aromatic hydrocarbon compounds of the aforementioned formula (III) to be used in the present invention include benzene, lower alkyl-substituted benzenes, lower alkoxyl-substituted benzenes, naphthalene, antracene, indane, lower alkyl-substituted indanes, tetralin, and lower alkyl-substituted tetralins. Among them, examples of the aromatic hydrocarbon compounds to which the process of the present invention is suitably applicable include benzene, 1,1,2,3,3-pentamethylindane represented by the following formula (a), 1,1,3-trimethyl-3-ethylindane represented by the following formula (b), and 1,1,3,3-tetramethylindane represented by the following formula (c):

(a)

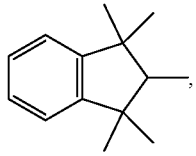

-continued

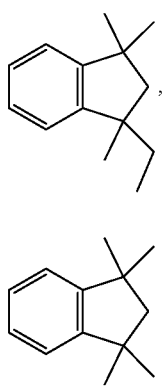

(b)

(c)

Examples of the Friedel-Crafts catalyst to be used include aluminum chloride, tin tetrachloride, titanium tetrachloride, zinc chloride, aluminum bromide, antimony trichloride, antimony pentachloride, and aluminum iodide, among which aluminum chloride, tin tetrachloride and titanium tetrachloride are preferred, among which aluminum chloride and tin tetrachloride are especially preferred. The Friedel-Crafts catalyst is used preferably in an amount of 0.5 to 1.5 mol, further preferably 0.7 to 1.1 mol, per mol of the arylalkanol of the aforementioned formula (II) or the aromatic hydrocarbon compound of the formula (III).

The alkylene oxide that may be used in the present invention is ethylene oxide or propylene oxide. The use of the alkylene oxide in a substantially equimolar amount to that of the aromatic hydrocarbon compound of the aformentioned formula (III) will suffice. Alternatively, however, either the alkylene oxide or the aromatic hydrocarbon compound may be used in an excessive amount.

The process of the present invention is characterized by comprising the step of adding an aqueous solution of formaldehyde having a concentration of 40 to 70 wt. % to the complex of the arylalkanol with the Friedel-Crafts catalyst to cyclize the arylalkanol. The complex of the arylalkanol with the Friedel-Crafts catalyst can be prepared by mixing the arylalkanol with the Friedel-Crafts catalyst. Accordingly, one mode of the process of the present invention comprises the step of mixing an arylalkanol according to the present invention with a Friedel-Crafts catalyst to prepare the complex of the arylalkanol with the Friedel-Crafts catalyst, and the step of adding an aqueous solution of formaldehyde having a concentration of 40 to 70 wt. % to the resulting complex of the arylalkanol with the Friedel-Craft's catalyst to cyclize the arylalkanol.

Alternatively, the complex of the arylalkanol with the Friedel-Crafts catalyst may be prepared by reacting the aromatic hydrocarbon compound of the formula (III) with an alkylene oxide in the presence of the Friedel-Crafts catalyst. Accordingly, another mode of the process of the present invention comprises the step of reacting an aromatic hydrocarbon compound according to the present invention with an alkylene oxide in the presence of a Friedel-Crafts catalyst to prepare a complex of the arylalkanol with the Friedel-Crafts catalyst, and the step of adding an aqueous solution of formaldehyde having a concentration of 40 to 70 wt. % to the resulting complex of the arylalkanol with the Friedel-Crafts catalyst to cyclize the arylalkanol. In this process, the second cyclization step may be taken even without isolation of the complex of the arylalkanol with the Friedel-Crafts catalyst. Accordingly, this process is a simple and economical one.

In the present invention, the reaction of the aromatic hydrocarbon compound with the alkylene oxide may be effected by any known method. This reaction is effected preferably in the presence of a solvent, further preferably in the presence of a chlorinated hydrocarbon solvent. Examples of the chlorinated hydrocarbon solvent include dichloromethane and dichloroethane, of which dichloromethane is most suitable. Further, this reaction may be effected at a temperature falling within the range of −40 to 0° C., preferably −30 to −20 C. When the reaction is effected at a temperature falling within this range, the rate of reaction is suitable while hardly involving the occurrence of side reactions, whereby a high yield can be attained. The reaction time is preferably about 30 minutes to about 5 hours.

In the present invention, the complex of the arylalkanol with the Friedel-Crafts catalyst, after being prepared, is mixed with an aqueous solution of formaldehyde having a concentration of 40 to 70 wt. %, preferably 40 to 55 wt. %, to cyclize the arylalkanol. As described above, the aqueous solution of formaldehyde may be added directly to the reaction mixture of the aromatic hydrocarbon compound according to the present invention with the alkylene oxide.

In the present invention, it is important to use an aqueous solution of formaldehyde having a concentration of 40 to 70 wt. When use is made of an aqueous solution of formaldehyde having a concentration lower than 40 wt. %, the operation of reaction is complicated. For example, when use is made of commercially available formalin (a 37 wt. % aqueous solution of formaldehyde), the reaction mixture gels to deteriorate the yield of reaction. On the other hand, when use is made of an aqueous solution of formaldehyde having a concentration exceeding 70 wt. %, formaldehyde is polymerized unfavorably. Further the use of formalin (a 37 wt. % aqueous solution of formaldehyde) in combination with paraformaldehyde instead of a high-concentration aqueous solution of formaldehyde, though conceivable, entails complicated operations because 2 kinds of starting materials are required. The amount of the aqueous solution of formaldehyde to be added is preferably such that the amount of formaldehyde is 0.7 to 1.1 mol per mol of the aromatic hydrocarbon compound of the aforementioned formula (III). The aqueous solution of formaldehyde is added to the complex of the arylalkanol with the Friedel-Crafts catalyst preferably at a temperature of −40° to 20° C., further preferably −30 to 5° C., especially preferably −30 to 0° C. The cyclization reaction may be effected at a temperature usually falling within the range of −30 to 30° C., preferably 0 to 30° C. When the reaction is effected at a temperature falling within this range, the rate of reaction is suitable while hardly involving the occurrence of side reactions, whereby a high yield can be attained. The reaction time is preferably about 1 hour to about 5 hours.

A preferred embodiment of the process of the present invention is as follows:

A Friedel-Crafts catalyst (e.g., aluminum chloride) and a chlorinated hydrocarbon solvent (e.g., dichloromethane) are added to an aromatic hydrocarbon compound of the aforementioned formula (III) under stirring. The resulting mixture is cooled to a temperature of about −40 to −20° C. Subsequently, a solution of an alkylene oxide in a chlorinated hydrocarbon solvent (e.g., dichloromethane) is dropwise added to the resulting mixture over 2 to 5 hours. During dropwise addition, the reaction system is maintained at a temperature of about −40 to −20° C. Thereafter, an aqueous solution of formaldehyde having a concentration of 40 to 70 wt. % is added to the resulting reaction mixture at a temperature of −30 to −20° C. over about 20 to 30 minutes.

The reaction is effected under stirring at a predetermined reaction temperature for 2 to 3 hours to complete the reaction. Water is added to the reaction product to remove the resulting water phase containing the Friedel-Crafts catalyst. The organic phase containing the product is washed with an aqueous solution of sodium hydroxide (caustic soda) having a concentration of 5 to 10 wt. % under a weakly basic condition. The organic phase containing the product is distilled to remove the solvent, followed by vacuum distillation. According to the foregoing procedure, the desired isochroman compound of the aforementioned formula (I) can be obtained in a high yield.

According to the process of the present invention, isochroman compounds, e.g., galaxolides, can be obtained in high yields and in such a high purity that they are substantially free from unreacted starting materials and any by-products (high-boiling substances). The reaction product obtained according to the present invention is a substance which has such an odor as to be well fit for use as a perfume.

Further, according to the process of the present Invention, introduction of hydrogen chloride gas for the reaction from outside is unnecessary, and unnecessary free hydrogen chloride gas is not substantially generated during the reaction. Accordingly, the process of the present invention is characterized in that it is remarkably simple in operations and involves little corrosion of equipment as compared with conventional processes involving introduction of hydrogen chloride gas from outside and conventional processes involving generation of hydrogen chloride gas during the reaction.

Furthermore, in comparison with another conventional process comprising the step of adding a compound having a free hydroxyl group as a deactivator to the reaction system in order to deactivate the catalyst before the addition of formaldehyde, the process of the present invention does not require such a deactivator and allows the reaction to be effected at a low temperature, whereby the post-treatment step can be simplified.

Moreover, according to the process of the present invention, isochroman compounds can be prepared in a single stage of reaction while using aromatic hydrocarbon compounds as the starting material. Thus, the process is simplified in steps as compared with conventional processes. Accordingly, the process of the present invention can be carried out very economically. Further, according to the process of the present invention, isochroman compounds can be prepared in high yields. In this aspect as well, the process of the present invention is very economical.

EXAMPLES

The following Examples will illustrate the present invention in more detail, but should not be construed as limiting the scope of the present invention.

In Examples, "%" is based on weight unless otherwise specified.

Example 1

75 g (0.398 mol) of 1,1,2,3,3-pentamethylindane was placed in a 500 ml four-necked flask equipped with a stirrer, a Liebig condenser having the upper portion thereof provided with a calcium chloride tube, and a thermometer, then stirred under a nitrogen stream at 300 rpm, and then mixed with 42.5 g (0.319 mol) of aluminum chloride and 17.3 g of dichloromethane at room temperature. The resulting solution was cooled to −20° C. A solution of 23.1 g (0.398 mol) of propylene oxide in 146.5 g of dichloromethane was dropwise added to the cooled solution over 4 hours. During this dropwise addition, the temperature of the reaction system was maintained at −20° C. to −30° C. After the completion of the dropwise addition, the resulting mixture was stirred at the same temperature for 15 minutes. Thereafter, 18 g (0.282 mol) of a 47% aqueous solution of formaldehyde was added to this mixture at 5° C. over 30 minutes. The resulting mixture was heated up to a temperature of 20° C. under stirring, and then further stirred at the same temperature for 2 hours and 30 minutes. 100 g of water was carefully dropwise added to the resulting mixture at a temperature of 30° C. or below. The resulting mixture was heated up to a temperature of 40° C. under stirring, and then further stirred at the same temperature for 1 hour. The resulting reaction mixture was allowed to stand still to effect phase separation. After the removal of the lower layer, the remaining organic phase was mixed with 50 g of a 10% aqueous solution of caustic soda. The resulting mixture was stirred at 40° C. for 1 hour, and then allowed to stand still to effect phase separation. After the removal of the lower layer, the remaining organic phase was distilled to remove the solvent. Subsequently, the residue was subjected to vacuum distillation (under 2 Torr) to obtain 67.2 g (0.26 mol) of 6-oxa-1,1,2,3,3,8-hexamethyl-2,3 5,6,7,8-hexahydro -1H-benz[f]indene as a fraction boiling at 138 to 148° C. (under 2 Torr). The yield was 65%.

Example 2

The reactions were effected in the same manner as in Example 1 except that 83.1 g of tin tetrachloride was used instead of 42.5 g of aluminum chloride. As a result, there was obtained 62.0 g (0.24 mol) of 6-oxa-1,1,2,3,3,8-hexamethyl -2,3,5,6,7,8-hexahydro-1H-benz[f]indene. The yield was 60%.

Example 3

31 g (0.398 mol) of benzene was put in a 500 ml four-necked flask equipped with a stirrer, a Liebig condenser having the upper portion thereof provided with a calcium chloride tube, and a thermometer, then stirred under a nitrogen stream at 300 rpm, and then mixed with 53 g (0.398 mol) of aluminum chloride and 17.3 g of dichlorometahne at room temperature. The resulting solution was cooled to −20° C. A solution of 17.5 g (0.398 mol) of ethylene oxide in 146.5 g of dichloromethane was dropwise added to the cooled solution over 4 hours. During this dropwise addition, the temperature of the reaction system was maintained at −20° C. to −30° C. After the completion of the dropwise addition, the resulting mixture was stirred at the same temperature for 15 minutes. Thereafter, 18 g (0.282 mol) of a 47% aqueous solution of formaldehyde was added to this mixture at 5° C. over 30 minutes. The resulting mixture was heated up to a temperature of 20° C. under stirring, and then further stirred at the same temperature for 2 hours and 30 minutes. 100 g of water was carefully added dropwise to the resulting mixture at a temperature of 30° C. or below. The resulting mixture was heated up to a temperature of 40° C. under stirring, and then further stirred at the same temperature for 1 hour. The resulting reaction mixture was allowed to stand still to effect phase separation. After the removal of the lower layer, the remaining organic phase was mixed with 50 g of a 10% aqueous solution of caustic soda. The resulting mixture was stirred at 40° C. for 1 hour, and then allowed to stand still to effect phase separation. After the removal of the lower layer, the remaining organic phase was distilled to remove the solvent. Subsequently, the residue was subjected to vacuum distillation (under 20 Torr) to obtain 37.4 g (0.278 mol) of isochroman as a fraction boiling at 105 to 106.5° C. (under 20 Torr). The yield was 70%.

Example 4

1,1,2,3, 3-Pentamethylindane was mixed with an equimolar amount of an anhydrous aluminum chloride powder. The resulting mixture was cooled to a temperature of −5° C. to −10° C. A solution of propylene oxide in 1,1,2,3,3-pentamethylindane was dropwise added to the cooled mixture. Immediately after the completion of the dropwise addition, the resulting bulk product was put into the same volume of iced water under stirring.

After being allowed to stand still to effect phase separation, the upper organic layer was sequentially washed with a 5% aqueous solution of caustic soda and an aqueous solution of sodium chloride. The unreacted 1,1,2,3,3-pentamethylindane was removed by vacuum distillation. The bottom was distilled to obtain 2-(1',1',2',3',3'-pentamethylindanyl -5')propan-1-ol.

50 g (0.203 mol) of 2-(1',1',2',3',3'-pentamethyl-indanyl-5') propan-1-ol and 50 g of dichloromethane were put in a 500 ml four-necked flask equipped with a stirrer, a Liebig condenser having the upper portion thereof provided with a calcium chloride tube, and a thermometer. The resulting solution was stirred, and then mixed with 21.7 g (0.16 mol) of aluminum chloride at room temperature. The resulting solution was cooled to 0° C. 13 g (0.203 mol) of a 47% aqueous solution of formaldehyde was added to the cooled solution at 0° C. over 30 minutes. The resulting mixture was heated up to a temperature of 20° C. under stirring, and then further stirred at the same temperature for 2 hours and 30 minutes. 100 g of water was carefully dropwise added to the resulting mixture at a temperature of 30° C. or below. The resulting mixture was heated up to a temperature of 40° C. under stirring, and then further stirred at the same temperature for 1 hour. The resulting reaction mixture was allowed to stand still to effect phase separation. After the removal of the lower layer, the remaining organic phase was mixed with 50 g of a 10% aqueous solution of caustic soda. The resulting mixture was stirred at 40° C. for 1 hour, and then mixed with ether. The resulting mixture was stirred and then allowed to stand still to effect phase separation. After the removal of the lower layer, the remaining organic phase was distilled to remove the solvent. Subsequently, the residue was subjected to vacuum distillation (under 2 Torr) to obtain 50 g (0.19 mol) of 6-oxa-1,1,2,3,3,8-hexamethyl -2,3,5,6,7, 8-hexahydro-1H-benz[f]indene as a fraction boiling at 138 to 148° C. (under 2 Torr). The yield was 95%.

Example 5

The reactions were effected in substantially the same manner as in Example 1 except that the 47% aqueous solution of formaldehyde was added at −20° C. As a result, 6-oxa-1,1,2,3,3,8-hexamethyl -2,3,5,6,7,8-hexahydro-1H-benz[f]indene was prepared in a yield of 70%.

Example 6

The reactions were effected in substantially the same manner as in Example 2 except that the 47% aqueous solution of formaldehyde was added at −20° C. As a result, 6-oxa-1,1,2,3,3,8-hexamethyl -2,3,5,6,7,8-hexahydro-1H-benz[f]indene was prepared in a yield of 63%.

Example 7

The reactions were effected in substantially the same manner as in Example 3 except that the 47% aqueous solution of formaldehyde was added at −20° C. As a result, isochroman was prepared in a yield of 74%.

Example 8

The reactions were effected in substantially the same manner as in Example 4 except that the 47% aqueous solution of formaldehyde was added at −20° C. As a result, 6-oxa-1,1,2,3,3,8-hexamethyl -2,3,5,6,7,8-hexahydro-1H-benz[f]indene was prepared in a yield of 97%.

Comparative Example 1

75 g (0.398 mol) of 1,1,2,3,3-pentamethylindane was put in a 500 ml four-necked flask equipped with a stirrer, a Liebig condenser having the upper portion thereof provided with a calcium chloride tube, and a thermometer, then stirred under a nitrogen stream at 300 rpm, and then mixed with 42.5 g (0.319 mol) of aluminum chloride and 17.3 g of dichloromethane at room temperature. The resulting solution was cooled to −20° C. A solution of 23.1 g (0.398 mol) of propylene oxide in 146.5 g of dichloromethane was dropwise added to the cooled solution over 4 hours. During this dropwise addition, the temperature of the reaction system was maintained at −20° C. to −30° C. After the completion of the dropwise addition, the resulting mixture was stirred at the same temperature for 15 minutes. Thereafter, 8.6 g (0.478 mol) of water was dropwise added to this mixture at −20° C., followed by the addition of 8.4 g (0.266 mol) of paraformaldehyde. The resulting mixture was heated up to room temperature (22° C.) under stirring, and then further stirred at the same temperature for 3 hours. 90 g of water was added to the resulting reaction mixture. The resulting mixture was heated up to a temperature of 40° C. under stirring, and then further stirred at the same temperature for 1 hour. The resulting reaction mixture was allowed to stand still to effect phase separation. After the removal of the lower layer, the remaining organic phase was mixed with 50 g of a 10% aqueous solution of caustic soda. The resulting mixture was stirred at 40° C. for 1 hour, and then allowed to stand still to effect phase separation. After the removal of the lower layer, the remaining organic phase was distilled to remove the solvent. Subsequently, the residue was subjected to vacuum distillation (under 2 Torr) to obtain 41.3 g (0.16 mol) of 6-oxa-1,1,2,3,3,8-hexamethyl -2,3,5,6, 7,8-hexahydro-1H-benz[f]indene as a fraction boiling at 138 to 148° C. (under 2 Torr). The yield was 40%.

Comparative Example 2

75 g (0.398 mol) of 1,1,2,3,3-pentamethylindane was put in a 500 m; four-necked flask equipped with a stirrer, a Liebig condenser having the upper portion thereof provided with a calcium chloride tube, and a thermometer, then stirred under a nitrogen stream at 300 rpm, and then mixed with 42.5 g (0.319 mol) of aluminum chloride and 17.3 g of dichloromethane at room temperature. The resulting solution was cooled to −20° C. A solution of 23.1 g (0.398 mol) of propylene oxide in 146.5 g of dichloromethane was dropwise added to the cooled solution over 4 hours. During this dropwise addition, the temperature of the reaction system was maintained at −20° C. to −30° C. After the completion of the dropwise addition, the resulting mixture was stirred at the same temperature for 15 minutes. Thereafter, 8.6 g (0.478 mol) of water was dropwise added to this mixture at −20° C. Subsequently, 8.4 g (0.266 mol) of formaldehyde formed by the thermal decomposition of paraformaldehyde was introduced into the resulting mixture while effecting the reaction at room temperature (22° C.) for 3 hours. 90 g of water was added to the resulting reaction mixture. The resulting mixture was heated up to a temperature of 40° C. under stirring, and then further stirred at the same temperature for 1 hour. The resulting reaction mixture was allowed to stand still to effect phase separation. After the removal of the lower layer, the remaining organic phase was mixed with 50 g of a 10% aqueous solution of caustic soda. The resulting mixture was stirred at 40° C. for 1 hour, and then allowed to stand still to effect phase separation. After the removal of the lower layer, the remaining organic phase was distilled to remove the solvent. Subsequently, the residue was subjected to vacuum distillation (under 2 Torr) to obtain 46.5 g (0.18 mol) of 6-oxa-1,1,2,3,3,8-hexamethyl-2,3,5,6,7,8-hexahydro-1H-benz[f]indene as a fraction boiling at 138 to 148° C. (under 2 Torr). The yield was 45%.

Comparative Example 3

75 g (0.398 mol) of 1,1,2,3,3-pentamethylindane was put in a 500 ml four-necked flask equipped with a stirrer, a Liebig condenser having the upper portion thereof provided with a calcium chloride tube, and a thermometer, then stirred under a nitrogen stream at 300 rpm, and then mixed with 42.5 g (0.319 mol) of aluminum chloride and 17.3 g of dichloromethane at room temperature. The resulting solution was cooled to −20° C. A solution of 23.1 g (0.398 mol) of propylene oxide in 146.5 g of dichloromethane was dropwise added to the cooled solution over 4 hours. During this dropwise addition, the temperature of the reaction system was maintained at −20° C. to −30° C. After the completion of the dropwise addition, the resulting mixture was stirred at the same temperature for 15 minutes. The resulting mixture was heated up to a temperature of 5° C. under stirring. Thereafter, 23 g (0.284 mol) of a 37% aqueous solution of formaldehyde was added to this mixture at the same temperature over 30 minutes. The resulting reaction mixture was heated up to a temperature of 20° C. under stirring, which was difficult because the reaction mixture became gel. 90 g of water was added to the resulting reaction mixture. The resulting mixture was heated up to a temperature of 40° C. under stirring, and then further stirred at the same temperature for 1 hour. The resulting reaction mixture was allowed to stand still to effect phase separation. After the removal of the lower layer, the remaining organic phase was mixed with 50 g of a 10% aqueous solution of caustic soda. The resulting mixture was stirred at 40° C. for 1 hour, and then allowed to stand still to effect phase separation. After the removal of the lower layer, the remaining organic phase was distilled to remove the solvent. Subsequently, the residue was subjected to vacuum distillation (under 2 Torr) to obtain 46.5 g (0.18 mol) of 6-oxa-1,1,2,3,3,8-hexamethyl-2,3,5,6,7,8-hexahydro-1H-benz[f]indene as a fraction boiling at 138 to 148° C. (under 2 Torr). The yield was 45%.

We claim:

1. A process for preparing isochroman compounds represented by the following general formula (I):

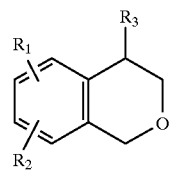

wherein $R_1$ and $R_2$ each stands for a hydrogen atom, a lower alkyl group or a lower alkoxyl group, or alternatively $R_1$ and $R_2$ are respectively bonded to adjacent carbon atoms with mutual bonding of $R_1$ and $R_2$ together with the carbon atoms respectively bonded to $R_1$ and $R_2$ to form a benzene ring, a naphthalene ring, or a $C_5$ or $C_6$ cycloalkane or cycloalkene which may have 1 to 6 lower alkyl groups; and $R_3$ stands for a hydrogen atom or a lower alkyl group;

comprising the step of adding an aqueous solution of formaldehyde having a concentration of 40 to 70 wt. % to a complex of an arylalkanol represented by the following general formula (II) with a Friedel-Crafts catalyst to cyclize said arylalkanol:

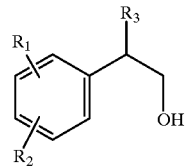

wherein $R_1$, $R_2$ and $R_3$ are each as defined above.

2. A process as claimed in claim 1, wherein said Friedel-Crafts catalyst is aluminum chloride, tin tetrachloride, or titanium tetrachloride.

3. A process as claimed in claim 1, which further comprises the step of mixing said arylalkanol of the formula (II) with said Friedel-Crafts catalyst to prepare said complex of said arylalkanol with said Friedel-Crafts catalyst.

4. A process as claimed in claim 1, which further comprises the step of reacting an aromatic hydrocarbon compound represented by the following general formula (III) with an alkylene oxide in the presence of said Friedel-Crafts catalyst to prepare said complex of said arylalkanol with said Friedel-Crafts catalyst:

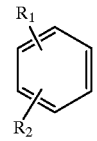

wherein $R_1$ and $R_2$ each stands for a hydrogen atom, a lower alkyl group or a lower alkoxyl group, or alternatively $R_1$ and $R_2$ are respectively bonded to adjacent carbon atoms with mutual bonding of $R_1$ and $R_2$ together with the carbon atoms respectively bonded to $R_1$ and $R_2$ to form a benzene ring, a naphthalene ring, or a $C_5$ or $C_6$ cycloalkane or cycloalkene which may have 1 to 6 lower alkyl groups.

5. A process as claimed in claim 4, wherein said aromatic carbon compound represented by the formula (III) is zene, 1,1,2,3,3-pentamethylindane represented by the following formula (a), 1,1,3-trimethyl-3-ethylindane resented by the following formula (b), or 1,1,3,3-tetramethylindane represented by the following formula (c):
(a)
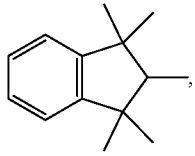
(b)
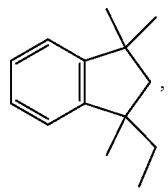
(c)
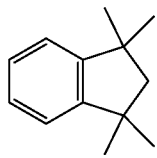
6. A process as claimed in claim 4, wherein said alkylene is ethylene oxide or propylene oxide.
* * * * *